(12) United States Patent
Viola

(10) Patent No.: US 9,675,377 B2
(45) Date of Patent: Jun. 13, 2017

(54) INCISIONAL HERNIA CUT LINE METHOD AND DEVICE

(71) Applicant: Covidien LP, Mansfield, MA (US)

(72) Inventor: Frank Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 316 days.

(21) Appl. No.: 14/371,526

(22) PCT Filed: May 28, 2013

(86) PCT No.: PCT/US2013/042815
§ 371 (c)(1),
(2) Date: Jul. 10, 2014

(87) PCT Pub. No.: WO2013/181124
PCT Pub. Date: Dec. 5, 2013

(65) Prior Publication Data
US 2015/0025556 A1    Jan. 22, 2015

Related U.S. Application Data

(60) Provisional application No. 61/652,514, filed on May 29, 2012.

(51) Int. Cl.
  *A61B 17/32*     (2006.01)
  *A61B 17/3209*   (2006.01)
  *A61B 17/3201*   (2006.01)

(52) U.S. Cl.
  CPC .... *A61B 17/32093* (2013.01); *A61B 17/3201* (2013.01); *A61B 17/3209* (2013.01)

(58) Field of Classification Search
  CPC ............ A61B 17/3201; A61B 17/3209; A61B 17/32093; A61B 2017/32096
  See application file for complete search history.

(56) References Cited

U.S. PATENT DOCUMENTS

| | | | |
|---|---|---|---|
| 4,832,045 A * | 5/1989 | Goldberger | ........ A61B 10/0233 600/567 |
| 5,002,562 A | 3/1991 | Oberlander | |
| 5,188,636 A | 2/1993 | Fedotov | |
| 5,500,000 A | 3/1996 | Feagin et al. | |
| 5,522,829 A | 6/1996 | Michalos | |
| 5,571,216 A | 11/1996 | Anderson | |
| 5,584,859 A | 12/1996 | Brotz | |
| 5,662,683 A | 9/1997 | Kay | |
| 5,904,696 A | 5/1999 | Rosenman | |
| 5,916,224 A | 6/1999 | Esplin | |

(Continued)

*Primary Examiner* — Ashley Fishback

(57) ABSTRACT

A method for making a non-linear incision includes forming a non-linear incision in tissue to improve post-operative adhesion of the incised tissue. In one aspect, a method for making a non-linear incision in tissue includes providing a surgical device including a housing and an end effector. The end effector is secured to the housing and includes a pair of jaws operable coupled to the housing. The jaws are disposed in substantial registration. The jaws may be oriented in substantially vertical registration or oriented in substantially horizontal registration. The method may include forming a non-linear incision in tissue with movement of tone or both of the jaws between approximated and unapproximated configurations. The movement may be horizontal or vertical.

15 Claims, 4 Drawing Sheets

(56) References Cited

U.S. PATENT DOCUMENTS

| | | | |
|---|---|---|---|
| 5,925,078 A | 7/1999 | Anderson | |
| 5,984,949 A | 11/1999 | Levin | |
| 5,993,475 A | 11/1999 | Lin et al. | |
| 7,361,185 B2 | 4/2008 | O'Malley et al. | |
| 2003/0114874 A1* | 6/2003 | Craig | A61B 17/320092 606/169 |
| 2005/0101952 A1* | 5/2005 | Lands | A61B 18/1445 606/51 |

* cited by examiner

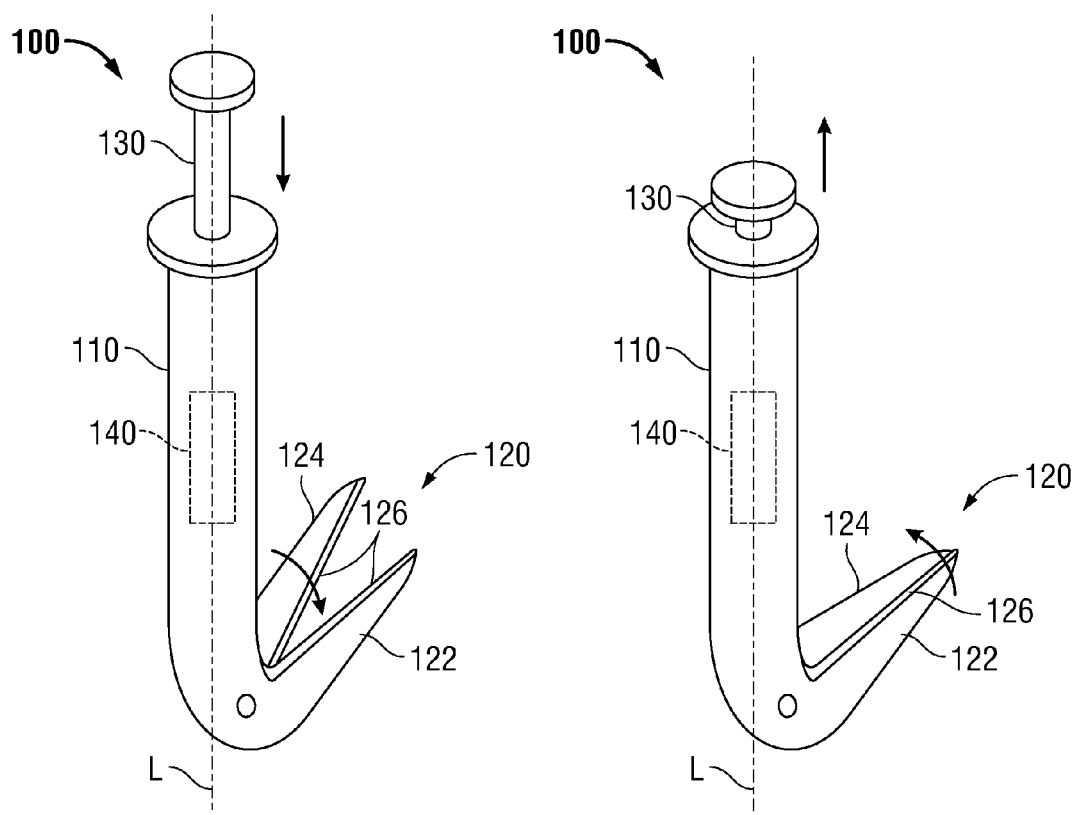
FIG. 2A  FIG. 2B

INCISIONAL HERNIA CUT LINE METHOD AND DEVICE

CROSS-REFERENCE TO RELATED APPLICATIONS

This application is a National Stage Application of PCT/US13/42815 under 35 USC §371 (a), which claims priority of U.S. Provisional Patent Application Ser. No. 61/652,514 filed May 29, 2012, the disclosures of each of the above-identified applications are hereby incorporated by reference in their entirety.

TECHNICAL FIELD

The present disclosure relates generally to incisional hernia prevention. In particular, the present disclosure relates to a medical device and method for providing improved post operative hernia resistance.

BACKGROUND OF RELATED ART

Puncture wounds, wounds that pierce through tissue, may result from trauma or may be intentionally created in order to provide access to a body cavity during surgical procedures. In this manner, the surgeon may introduce a surgical instrument such as a grasper, scissor, clip applier, stapler or any other surgical instrument which may be necessary during the particular surgical procedure. Once the procedure is complete, it is necessary to close the wound in order to protect against undesirable conditions. A hernia, for example, is a protrusion of a tissue, structure, or part of an organ through injured muscle tissue or an injured membrane by which the tissue, structure, or organ is normally contained. Some examples of hernias include: abdominal hernias, diaphragmatic hernias and hiatal hernias (for example, para-esophageal hernia of the stomach), pelvic hernias, for example, obturator hernia, anal hernias, hernias of the nucleus pulposus of the intervertebral discs, intracranial hernias, and Spigelian hernias. In this respect, a continuing need exists for a device and a method that enables maximum post operative healing of tissue (e.g., the skin) for enhanced hernia resistance.

SUMMARY

Accordingly, a method for making a non-linear incision in tissue is disclosed and includes the step of forming a non-linear incision in tissue to improve post-operative adhesion of the incised tissue.

In one aspect, a method for making a non-linear incision in tissue includes the step of providing a surgical device including a housing and an end effector. The end effector is secured to the housing and includes a pair of jaws operably coupled to the housing.

The method may include forming a non-linear incision in tissue with vertical movement of one or both of the jaws between approximated and unapproximated configurations where the pair of jaws is disposed in substantial vertical registration.

The method may involve forming a non-linear incision in tissue with horizontal movement of one or both of the jaws between approximated and unapproximated configurations where the pair of jaws is disposed in substantial horizontal registration.

The method may involve the step of articulating the pair of jaws to form the incision. One step may include rotating the pair of jaws to form the incision.

The method may involve the step of forming the non-linear incision so that the incision is substantially sinusoidal. One step may include forming the non-linear incision so that the incision includes a plurality of alternating peaks and valleys. The method may involve forming the non-linear incision so that the incision includes a plurality of contiguous substantially U-shaped incisions. One step may involve forming the non-linear incision so that the incision includes a plurality of contiguous substantially V-shaped incisions. The method may include forming the non-linear incision so that non-linear incision provides resistance to post-operative hernias upon healing.

BRIEF DESCRIPTION OF THE DRAWINGS

Various embodiments of the present disclosure will be described herein below with reference to the figures wherein:

FIGS. 2A and 2B are side perspective views of the presently disclosed surgical device showing the end effector thereof being positioned between approximated and unapproximated configurations.

DETAILED DESCRIPTION

Figure 1:
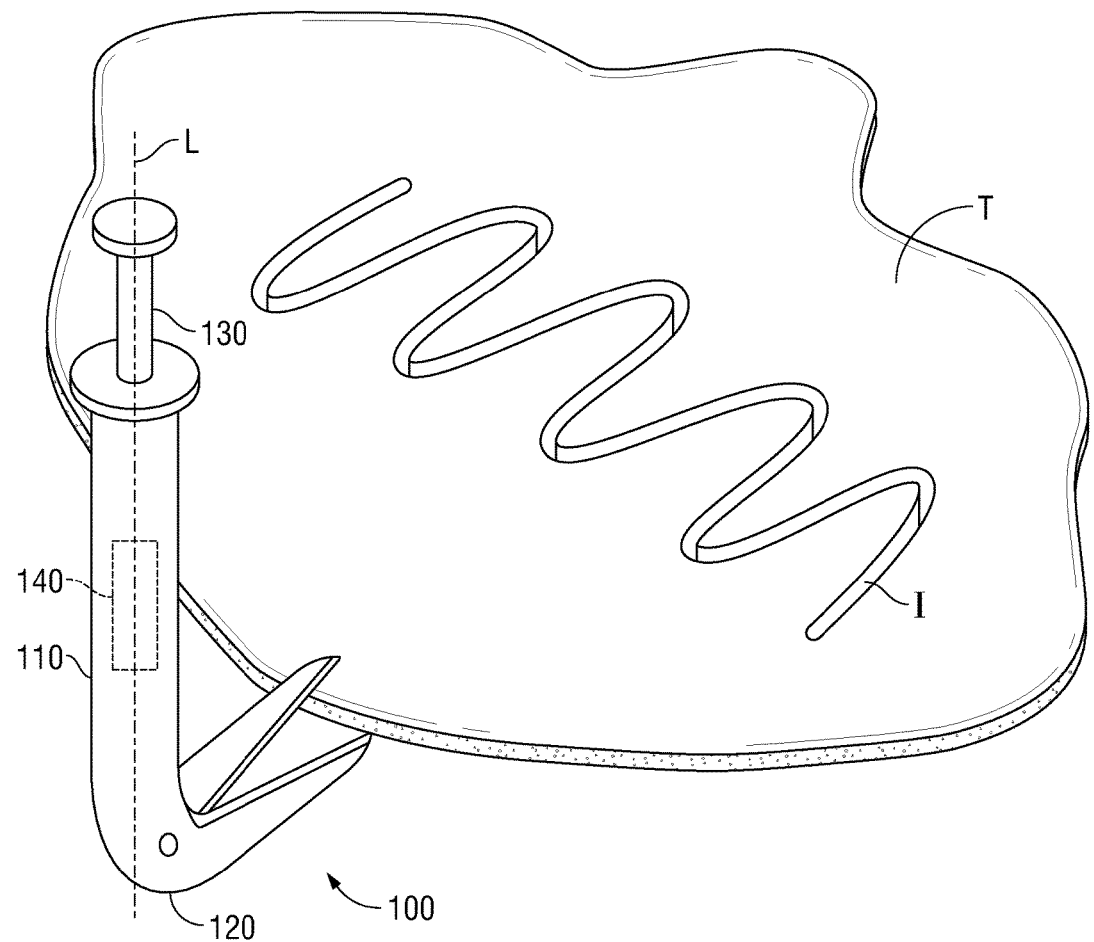
FIG. 1 is a perspective view of one embodiment of a surgical device and an incision formed in tissue by the presently disclosed surgical device in accordance with the principles of the present disclosure.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is farther from the user. In the following description, well-known functions or constructions are not described in detail to avoid obscuring the present disclosure in unnecessary detail.

Referring now to FIG. 1, one embodiment of the presently disclosed surgical device for making a non-linear incision is generally referred to as 100. Surgical device 100 includes a housing 110, an end effector 120, one or more controls 130, and a drive assembly 140. The housing 110 defines a longitudinal axis "L" which extends therethrough.

As illustrated in FIGS. 2A and 2B, the end effector 120 is operably coupled to the housing 110 and the drive assembly 140. The end effector 120 may be positioned between approximated (FIG. 2B) and unapproximated positions (FIG. 2A) upon actuation of the one or more controls 130. The end effector 120 includes first and second jaws 122, 124.

One or both of the first and second jaws 122, 124 include one or more cutting edges 126 that may be used to form a non-linear incision "I" in tissue when cutting tissue "T" (FIG. 1). The non-linear incision "I" will be described in greater detail below.

Referring now to FIGS. 2A and 2B, the one or more controls 130 are operably coupled to the housing 110 and are movable between first and second longitudinal positions. As illustrated in FIGS. 2A-2B, the one or more controls 130 are operably coupled to the drive assembly 140 and are axially movable along longitudinal axis "L" to move one or both of the first and second jaws 122, 124 between the approximated and unapproximated positions via the drive assembly 140.

Figure 3A:
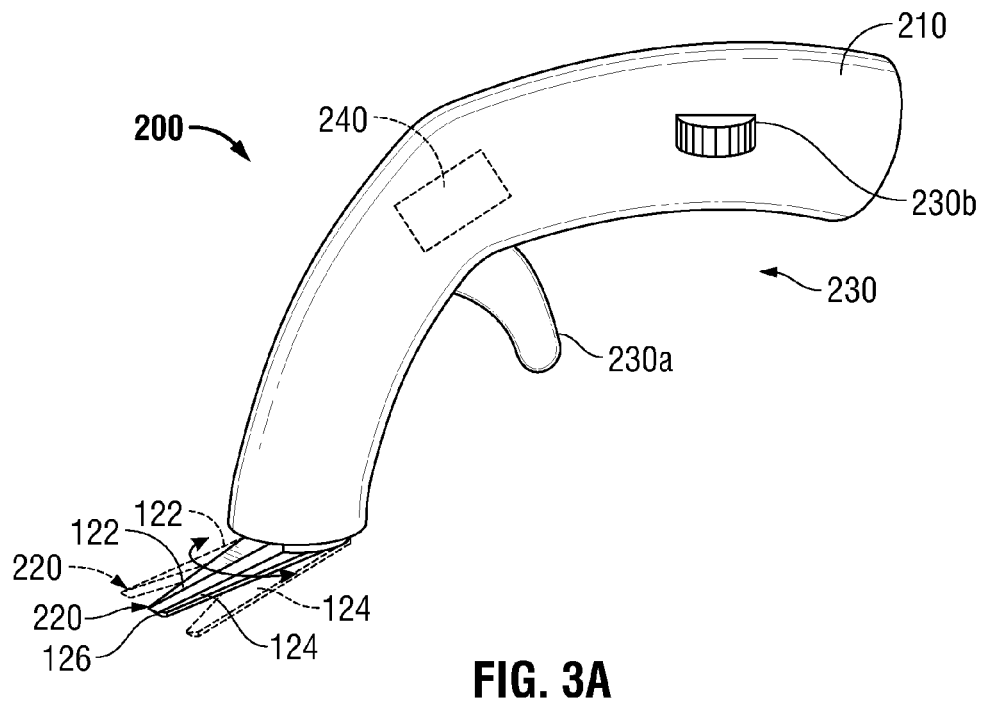
FIG. 3A is a side perspective view of another embodiment of the presently disclosed surgical device in accordance with the present disclosure.

With reference to FIG. 3A, another embodiment of the presently disclosed surgical device for making a non-linear incision is generally referred to as 200. Surgical device 200 is similar to surgical device 100 and is described herein only to the extent necessary to describe the differences in construction and operation thereof. Surgical device 200 includes housing 210, end effector 220, one or more controls 230, and a drive assembly 240. The end effector 220 includes first and second jaws 122, 124. One or both of the first and second jaws 122, 124 include one or more cutting edges 126. The first and second jaws 122, 124 are disposed in substantial horizontal registration. More particularly, the first and second jaws are positioned slightly longitudinally offset so that the one or more cutting edges 126 approximate in a manner sufficient to cut tissue "T" on opposed sides of the tissue "T." In this respect, horizontal movement of one or both of the jaws 122, 124 between approximated and unapproximated configurations (the unapproximated configuration being shown in phantom), in response to actuation of the one or more controls 230, enables a user to form a non-linear incision "I" in tissue "T."

Figure 3B:
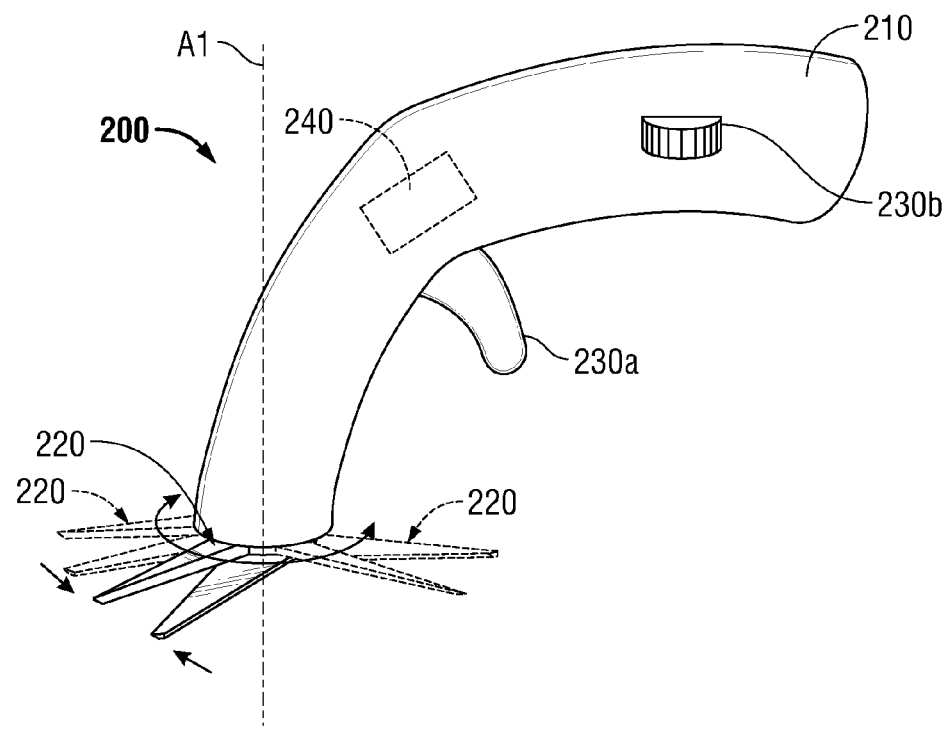
FIG. 3B is a side perspective view of the surgical device of FIG. 3A illustrating various orientations of the end effector of the surgical device of FIG. 3A.

With continued reference to FIG. 3A, the surgical device 200 includes a first control 230a that moves one or both of the first and second jaws 122, 124 between approximated and unapproximated positions via the drive assembly 240. As best shown in FIG. 3B, the surgical device 200 also includes a second control 230b that rotates the end effector 220, including both the first and second jaws 122, 124, about a an axis "A1" defined through the housing 210 at a proximal end of the jaws 122, 124. Actuation of the second control 230b enables a user to position the end effector 220 in any suitable angular orientation. For example, the first and second jaws 122, 124 may be rotated between 0-360 degrees about axis "A1" to achieve any desired angular orientation that facilitates the formation of a non-linear incision "I" in tissue "T."

Figure 4A:
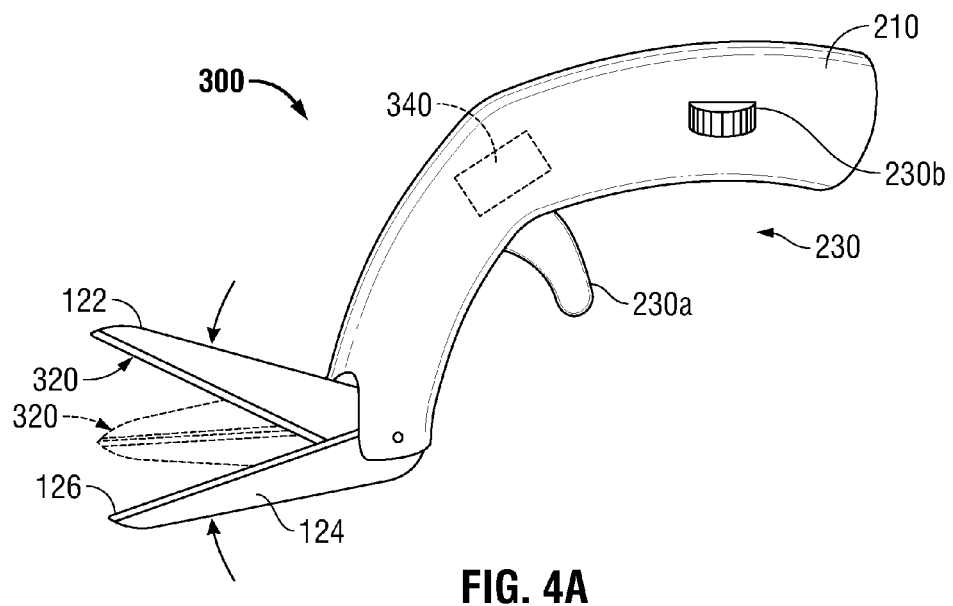
FIG. 4A is a side perspective view of yet another embodiment of the presently disclosed surgical device in accordance with the present disclosure.

FIG. 4A is a perspective view of another embodiment of a surgical device which is generally referred to as 300. Surgical device 300 is similar to surgical device 200 and is described herein only to the extent necessary to describe the differences in construction and operation thereof. Surgical device 300 includes housing 210, end effector 320, one or more controls 230, and a drive assembly 340. The end effector 320 includes first and second jaws 122, 124. One or both of the first and second jaws 122, 124 include one or more cutting edges 126. The first and second jaws 122, 124 are disposed in substantial vertical registration. More particularly, the first and second jaws are positioned slightly laterally offset so that the one or more cutting edges 126 approximate in a manner sufficient to cut tissue "T" on opposed sides of the tissue "T." In this respect, vertical movement of one or both of the jaws 122, 124 between approximated and unapproximated configurations (the approximated configuration being shown in phantom), in response to actuation of the one or more controls 230, enables a user to form a non-linear incision "I" in tissue "T."

Figure 4B:
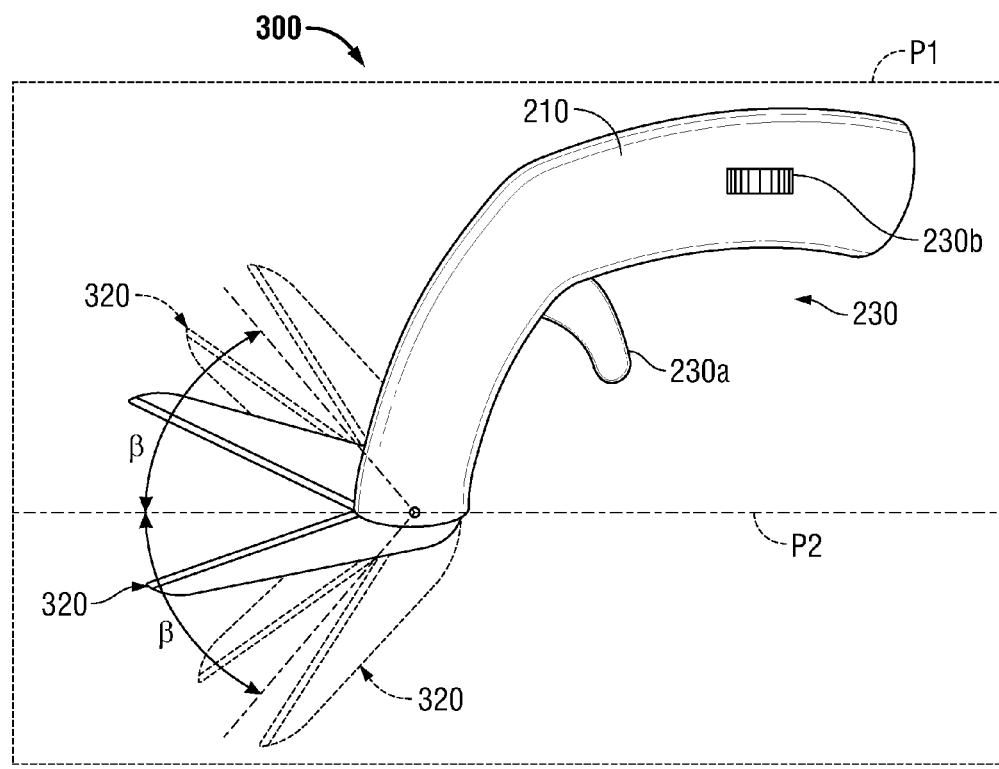
FIG. 4B is a side view of the surgical device of FIG. 4A illustrating various orientations of the end effector of the surgical device of FIG. 4A.

As best depicted in FIG. 4A, the surgical device 300 includes a first control 230a that moves one or both of the first and second jaws 122, 124 between approximated and unapproximated positions via the drive assembly 340. With reference to FIG. 4B, the surgical device 300 also includes a second control 230b that articulates the end effector 320, including both the first and second jaws 122, 124, about a transverse plane "P2" that is perpendicular to a sagittal plane "P1" defined centrally through housing 210 to enable a user to achieve a desired angular orientation of the end effector 320 relative to the transverse plane "P2." Transverse plane "P2" is oriented adjacent the end effector 320. In this regard, the first and second jaws 122, 124 may be vertically articulated at any angle $\beta$, particularly 0-270 degrees, relative to the transverse plane "P2" to achieve any desired angular orientation that facilitates the formation of a non-linear incision "I" in tissue "T." The first and second jaws 122, 124 may be positioned along an outer surface of the housing 210 such that the first angle $\beta$ is between 0-360 degrees, where desired.

Any one of the presently disclosed surgical devices may be used to form a non-linear open curve incision "I" in tissue "T." The non-linear incision "I" may be cut so that the incision "I" is substantially sinusoidal. The non-linear incision "I" may be cut to include a plurality of alternating peaks and valleys. Further, the incision "I" may include a plurality of contiguous substantially U-shaped incisions. The non-linear incision "I" may also be cut so that the incision "I" includes a plurality of contiguous substantially V-shaped incisions. The non-linear incision "I" may also be cut so that the non-linear incision provides resistance to post-operative hernias upon healing.

The formation of one or more of any of these non-linear incisions in tissue increases the surface area for adhesion and, thus, improves post-operative adhesion of the incised tissue, in particular, when the separated tissues formed by incising the tissue are post-operatively joined by e.g., suture, adhesive, staple, etc. to facilitate healing. In this regard, the non-linear incisions form a stronger seal upon healing than a linear incision due to the increased surface area.

Indeed, the presently disclosed surgical devices may be utilized in any cosmetic, endoscopic or laparoscopic methods. It should also be noted that a scalpel, knife, or any other suitable cutting device known in the art may be used to form a non-linear incision in tissue consistent with the principles of the present disclosure.

While the above description contains many specifics, these specifics should not be construed as limitations on the scope of the disclosure, but merely as exemplifications of embodiments thereof. Those skilled in the art will envision many other possibilities within the scope and spirit of the disclosure as defined by the claims appended hereto.

What is claimed is:

1. A method for making a non-linear incision in tissue, the method comprising:
   providing a surgical device including a housing and an end effector, the end effector being secured to the housing and including a pair of jaws operably coupled to the housing, the pair of jaws being disposed in substantial registration;
   forming a non-linear incision in tissue with movement of at least one of the jaws between approximated and unapproximated configurations to improve post-operative adhesion of the incised tissue; and forming the non-linear incision so that the non-linear incision includes a plurality of contiguous substantially V-shaped incisions.

2. The method of claim 1, further comprising forming the non-linear incision in tissue with vertical movement of at least one of the jaws between approximated and unapproximated configurations, wherein the pair of jaws is disposed in substantial vertical registration.

3. The method of claim 1, further comprising forming the non-linear incision in tissue with horizontal movement of at least one of the jaws between approximated and unapproximated configurations, wherein the pair of jaws is disposed in substantial horizontal registration.

4. The method of claim 1, further comprising forming the non-linear incision so that the non-linear incision is substantially sinusoidal.

5. The method of claim 1, further comprising forming the non-linear incision so that the non-linear incision includes a plurality of alternating peaks and valleys.

6. The method of claim 1, further comprising forming the non-linear incision so that the non-linear incision includes a plurality of contiguous substantially U-shaped incisions.

7. The method of claim 1, further comprising forming the non-linear incision so that the non-linear incision provides resistance to post-operative hernias upon healing.

8. The method of claim 1, further comprising articulating the pair of jaws to form the non-linear incision.

9. The method of claim 1, further comprising rotating the pair of jaws to form the non-linear incision.

10. The method of claim 1, further comprising forming the plurality of contiguous substantially V-shaped incisions in an open curve.

11. A method for making a non-linear incision in tissue, the method comprising:
    forming a non-linear incision in tissue to improve post-operative adhesion of the incised tissue; and
    forming the non-linear incision so that the non-linear incision includes a plurality of contiguous V-shaped incisions formed in an open curve.

12. The method of claim 11, further comprising forming the non-linear incision so that the non-linear incision is substantially sinusoidal.

13. The method of claim 11, further comprising forming the non-linear incision so that the non-linear incision includes a plurality of alternating peaks and valleys.

14. The method of claim 11, further comprising forming the non-linear incision so that the non-linear incision includes a plurality of contiguous substantially U-shaped incisions.

15. The method of claim 11, further comprising forming the non-linear incision so that the non-linear incision provides resistance to post-operative hernias upon healing.

* * * * *